United States Patent [19]
Hansenne et al.

[11] Patent Number: 6,143,282
[45] Date of Patent: Nov. 7, 2000

[54] PHOTOPROTECTIVE/COSMETIC COMPOSITIONS COMPRISING BENZOTRIAZOLE-SUBSTITUTED SILICON SUNSCREENS AND CINNAMIC/SALICYLIC ACID SOLUBILIZING AGENTS THEREFOR

[75] Inventors: Isabelle Hansenne, Westfield, N.J.; Martin Josso, Paris; Karine De Chabannes, Orleans, both of France

[73] Assignee: Societe L'Oreal S.A., Paris, France

[21] Appl. No.: 09/397,513

[22] Filed: Sep. 17, 1999

[30]  Foreign Application Priority Data

Sep. 25, 1998 [FR] France ..................... 98 12042

[51] Int. Cl.⁷ ............................. A61K 7/42; A61K 7/44; A61K 7/00
[52] U.S. Cl. ............................. 424/59; 424/60; 424/400; 424/401
[58] Field of Search ................ 424/59, 60, 400, 424/401

[56]  References Cited

FOREIGN PATENT DOCUMENTS 0711779  11/1994  European Pat. Off. .
0742003  11/1996  European Pat. Off. .

Primary Examiner—Shelley A. Dodson
Attorney, Agent, or Firm—Burns, Doane, Swecker & Mathis, L.L.P.

[57]  ABSTRACT

Topically applicable cosmetic/dermatological sunscreen compositions well suited for the UV-photoprotection of human skin and/or hair against the damaging effects of UV-A and UV-B irradiation, particularly solar radiation, comprise (i) a UV-photoprotecting effective amount of at least one solubilized organolipophilic silicon compound, whether solid silane or organopolysiloxane, bearing a benzotriazole function substituent and (ii) an amount of at least one cinnamic acid sunscreen compound and/or at least one salicylic acid sunscreen compound effective to (substantially) dissolve said at least one organolipophilic silicon compound.

36 Claims, No Drawings

PHOTOPROTECTIVE/COSMETIC COMPOSITIONS COMPRISING BENZOTRIAZOLE-SUBSTITUTED SILICON SUNSCREENS AND CINNAMIC/SALICYLIC ACID SOLUBILIZING AGENTS THEREFOR

CROSS-REFERENCE TO PRIORITY APPLICATION

This application claims priority under 35 U.S.C. §119 of FR-98/12042, filed Sep. 25, 1998, hereby expressly incorporated by reference.

CROSS-REFERENCE TO COMPANION APPLICATION

Copending application Ser. No. 09/397,514, filed concurrently herewith and assigned to the assign hereof.

BACKGROUND OF THE INVENTION

1. Technical Field of the Invention

The present invention relates to novel cosmetic compositions for topical application, in particular for the photoprotection of the skin and/or the lips and/or superficial body growths/hair against ultraviolet radiation (such compositions hereinafter simply being designated antisun or sunscreen compositions), and to the use of same for the cosmetic applications indicated above.

More especially, this invention relates to novel cosmetic compositions exhibiting improved photoprotective capacity, comprising, formulated into a cosmetically acceptable support therefor: (i) at least one silicon compound bearing a benzotriazole function substituent and constituting a lipophilic organic sunscreen, and (ii) a solubilizing amount of at least one cinnamic/salicylic acid liquid UV-screening agent.

2. Description of the Prior Art

It is known to this art that light radiation of wavelengths of from 280 nm to 400 nm permits tanning of the human epidermis and that light radiation of wavelengths of from 280 to 320 nm, i.e., UV-B irradiation, causes skin burns and erythema which may be harmful to the development of a natural tan; this UV-B radiation should thus be screened from the skin.

It is also known to this art that UV-A radiation, of wavelengths of from 320 to 400 nm, promotes tanning of the skin, but is also liable to induce an adverse change therein, especially in the case of sensitive skin or skin which is continually exposed to solar radiation. UV-A rays in particular cause a loss of elasticity of the skin and the appearance of wrinkles, promoting a premature aging of the skin. Such irradiation promotes triggering of the erythemal reaction or amplifies this reaction in certain individuals and may even be the cause of phototoxic or photoallergic reactions. It is thus desirable to also screen out UV-A radiation.

Many and varied cosmetic compositions for the photoprotection (UV-A and/or UV-B) of the skin are known to this art.

For a variety of reasons, related in particular to better comfort during use (softness, emollience, ease of application, etc.), the known sunscreen compositions are generally formulated as oil-in-water emulsions, i.e., cosmetically acceptable vehicle comprising a continuous dispersing aqueous phase and a discontinuous dispersed oily phase.

Too, these known sunscreen compositions contain, in various concentrations and depending on the nature of the pharmaceutical form selected, one or more standard lipophilic and/or hydrophilic organic screening agents capable of selectively absorbing harmful UV radiation, these screening agents (and the amounts thereof) being selected as a function of the desired protection factor (the protection factor (PF) being expressed mathematically as the ratio of the irradiation time required to reach the erythema-forming threshold with the UV screening agent to the time required to reach the erythema-forming threshold without UV screening agent).

Lipophilic UV organic screening agents which are particularly advantageous in antisun cosmetics and which are highly active both in the UV-A range and in the UV-B range are described in EP-A-0,392,883; EP-A-0,660,701; EP-A-0,708,108; EP-A-0,711,778; EP-A-711,779.

These are silanes or polyorganosiloxanes substituted by a benzotriazole function. They present the particular feature but also the drawback of being solid at room temperature. Consequently, including same in an antisun cosmetic composition entails certain constraints as regards their formulation and implementation, in particular as regards determining solvents for properly dissolving them. In this respect, oils are typically selected such as esters, and more particularly $C_{12}$–$C_{15}$ alkyl benzoates ("Finsolv TN" marketed by Finetex), or triglycerides and in particular $C_8$–$C_{12}$ fatty acid triglycerides ("Miglyol 812" marketed by Huls), or monoalcohols or polyols such as ethanol, as well as mixtures thereof. Although providing solubilizing properties with respect to the aforesaid screening agents, these solvents nevertheless present the drawback of themselves having no intrinsic activity as regards screening out UV radiation, whether UV-A or UV-B irradiation.

SUMMARY OF THE INVENTION

It has now unexpectedly and surprisingly been determined that UV screening agents of the cinnamic acid derivative type and/or UV screening agents of the salicylic acid derivative type are particularly desirable and noteworthy solvents for the solid screening agents described above, namely, silicon compounds bearing a benzotriazole functional group substituent. It should thus be appreciated that cinnamic acid derivatives and salicylic acid derivative are liquid lipophilic screening agents which are already known for their sunscreen activity in the UV-B range, but their solubilizing properties with respect to the above solid screening agents had yet to be determined.

The advantages presented by this invention are twofold, in the sense that silicon compounds bearing a benzotriazole functional group substituent or mixture thereof are dissolved in a solvent other than those previously known, which is always advantageous per se, and in that the total amount of screening agents is at the same time increased to obtain, in the final antisun composition, a substantial increase in the level of protection attributed thereto.

Thus, in the present invention features novel cosmetic compositions, in particular antisun/sunscreen compositions, which comprise, formulated into a cosmetically acceptable support therefor, (i) a dissolved screening system comprising at least one silicon derivative bearing a benzotriazole functional group substituent and (ii) a solubilizing screening system comprising a least one cinnamic acid derivative and/or at least one salicylic acid derivative, said solubilizing screening system being present in an amount which is sufficient by itself to dissolve all of said dissolved screening system.

The present invention also features converting the above compositions into cosmetic products for the protection of the skin and/or hair against ultraviolet radiation, in particular solar radiation.

This invention also features a cosmetic regime/regimen for the protection of the skin and/or hair against ultraviolet radiation, in particular solar radiation, comprising topically applying thereto, for such period of time as required to elicit the desired response, an effective photoprotecting amount of a composition as above described.

Accordingly, the present invention also features the preparation of cosmetic compositions for the protection of the skin and/or hair against UV radiation, comprising formulating at least one cinnamic acid and/or at least one salicylic acid sunscreen derivative as solubilizing screening system in a sufficient amount, to dissolve, by itself alone, at least one solid UV screening agent of the silicon derivative substituted with a benzotriazole functional group type.

DETAILED DESCRIPTION OF BEST MODE AND SPECIFIC/PREFERRED EMBODIMENTS OF THE INVENTION

More particularly according to the present invention, the silicon compounds substituted by a benzotriazole function are preferably silanes or siloxanes containing a benzotriazole function comprising at least one structural unit of formula (1) below:

$$O_{(3-a)/2}Si(R_1)_a—G \quad (1)$$

in which $R_1$ is an optionally halogenated $C_1-C_{10}$ alkyl radical, or a phenyl or trimethylsilyloxy radical; a is an integer ranging from 0 to 3, inclusive; and the symbol G is a monovalent radical directly bonded to a silicon atom and having the formula (2) below:

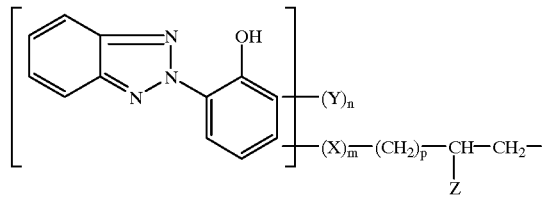

(2)

in which the radicals Y, which may be identical or different, are each a $C_1-C_8$ alkyl radical, a halogen atom, or a $C_1-C_4$ alkoxy radical, with the proviso that, in the latter instance, two adjacent groups Y on the same aromatic ring member can together form an alkylidenedioxy group wherein the alkylidene group contains 1 or 2 carbon atoms; X is O or NH; Z is hydrogen or a $C_1-C_4$ alkyl radical; n is an integer ranging from 0 to 3, inclusive; m is 0 or 1; and p is an integer ranging from 1 to 10, inclusive.

These compounds are described, in particular, in EP-A-0,392,883; EP-A-0,660,701; EP-A-0,708,108; EP-A-0,711,778; EP-A-711,779.

Preferably, the silicon derivatives according to the present invention belong to the general family of benzotriazole silicones which is described in EP-A-0,660,701.

One family or class of benzotriazole silicones which is particularly suitable according to the present invention is that which combines the compounds corresponding to formula (5) or (6) below:

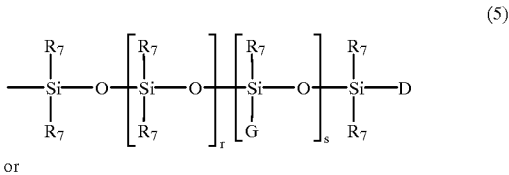

(5)

or

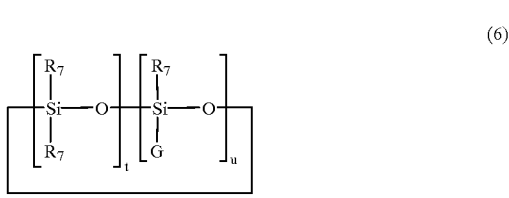

(6)

in which the radicals $R_7$, which may be identical or different, are each a $C_1-C_{10}$ alkyl, phenyl, 3,3,3-trifluoropropyl or trimethylsilyloxy radical, at least 80% by number of the radicals $R_7$ being methyl radicals; the radicals D, which may be identical or different, are each a radical $R_7$ or the radical G; r is an integer ranging from 0 to 50, inclusive, and s is an integer ranging from 0 to 20 inclusive, and if s=0, at least one of the two radicals D is a radical G; u is an integer ranging from 1 to 6, inclusive, and t is an integer ranging from 0 to 10, inclusive, with the proviso that t+u is greater than or equal to 3; and the radical G has the formula (2) above.

As will be seen from formula (2) above, bonding of the radical —(X)$_m$—(CH$_2$)$_p$—CH(Z)—CH$_2$— to the benzotriazole nucleus, which thus ensures attachment of said benzotriazole nucleus to a silicon atom of the silicone chain, may be at all of the available positions of the two aromatic rings of the benzotriazole:

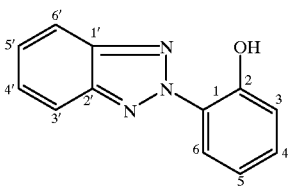

Preferably, this bonding is at position 3, 4, 5 (aromatic ring bearing the hydroxyl function) or 4' (benzene ring adjacent to the triazole ring), and even more preferably is at position 3, 4 or 5. In a preferred embodiment of the invention, the bonding is at position 3.

Similarly, attachment of the substituent unit or units Y may be at all the other available positions in the benzotriazole. However, preferably, this bonding is at position 3, 4, 4', 5 and/or 6. In a preferred embodiment of the invention, attachment of the unit Y is at position 5.

In formulae (5) and (6) above, the alkyl radicals may be linear or branched and selected in particular from among methyl, ethyl, n-propyl, isopropyl, n-butyl, isobutyl, tert-butyl, n-amyl, isoamyl, neopentyl, n-hexyl, n-heptyl, n-octyl, 2-ethylhexyl and tert-octyl radicals. The preferred alkyl radicals $R_7$ according to the invention are methyl, ethyl, propyl, n-butyl, n-octyl and 2-ethylhexyl radicals. Even more preferably, the radicals $R_2$ are all methyl radicals.

Among the compounds of formula (5) or (6) above, preferred are those corresponding to formula (5), namely, diorganosiloxanes containing a short linear chain.

Among the compounds of formula (5) above, preferred are those for which the radicals D are both radicals $R_7$.

Among the linear diorganosiloxanes within the scope of the present invention, particularly preferred are the random derivatives or well-defined block derivatives having at least one, and even more preferably all, of the following characteristics:

D is a radical $R_7$;

$R_7$ is alkyl and even more preferably is methyl;

r ranges from 0 to 15, inclusive; s ranges from 1 to 10, inclusive;

n is not zero and preferably is equal to 1, and Y is then selected from among methyl, tert-butyl and $C_1$–$C_4$ alkoxy;

Z is hydrogen or methyl;

m=0 or [m=1 and X=O];

p is equal to 1.

One family or class of benzotriazole silicones which is particularly preferred is that having the general formula (7) below:

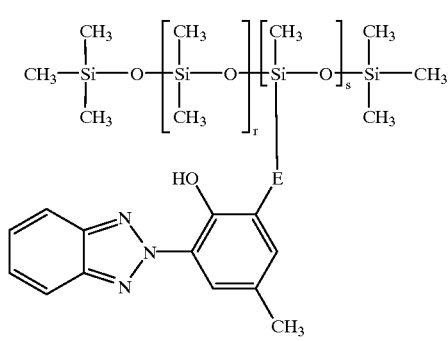

(7)

in which $0 \leq r \leq 10$; $1 \leq s \leq 10$; and E is the divalent radical:

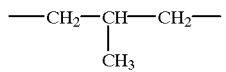

In a particularly preferred embodiment of the invention, the benzotriazole silicone is the compound (hereinafter referred to as compound (a)) having the following formula:

compound (a)

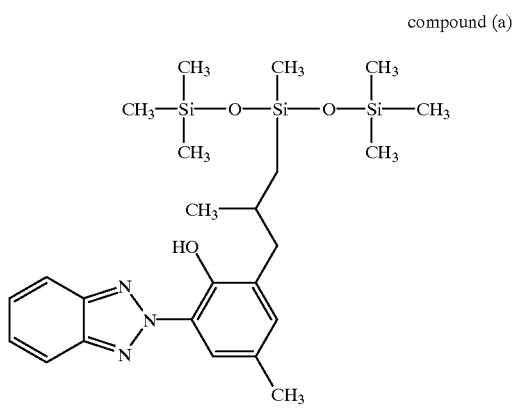

Processes which are suitable for the preparation of the compounds of formulae (1), (5), (6) and (7) are described, in particular, in U.S. Pat. Nos. 3,220,972, 3,697,473, 4,340,709, 4,316,033 and 4,328,346 and in EP-A-0,392,883 and EP-A-0,742,003.

The screening silicon compounds bearing a benzotriazole substituent are advantageously present in the compositions according to the invention in amounts ranging from 0.1% to 20%, preferably ranging from 0.2% to 15%, by weight, again relative to the total weight of the composition. According to an essential characteristic of the present invention, these compounds, whether alone or in admixture, should be present in the final composition in a fully, or substantially fully, dissolved form.

Exemplary cinnamic acid sunscreen compounds which are very well suited as solubilizing agents according to the present invention are isopentyl 4-methoxycinnamate, 2-ethylhexyl 4-methoxycinnamate, methyl diisopropylcinnamate, isoamyl 4-methoxycinnamate or diethanolamine 4-methoxycinnamate.

Among the above cinnamic acid derivatives, very particularly preferred is 2-ethylhexyl p-methoxycinnamate, marketed under the trademark "Parsol MCX" by Givaudan; this screening agent thus corresponds to the following structural formula:

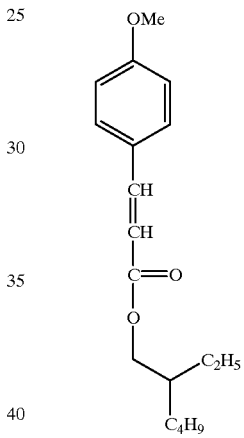

And exemplary salicylic acid sunscreen compounds which are also very well suited as solubilizing agents according to this invention are homomenthyl salicylate, 2-ethylhexyl salicylate, triethanolamine salicylate or 4-isopropylbenzyl salicylate.

Among the above salicylic acid derivatives, particularly preferred is homomenthyl salicylate, also known as homosalate, such as the product commercially available under the trademark "Kemester HMS" from Witco. It corresponds to the following structural formula:

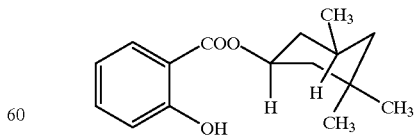

Also among the above salicylic acid derivatives, even more particularly preferred is octyl salicylate, marketed under the trademark "Uvinol O-18" by BASF, and corresponding to the following structural formula:

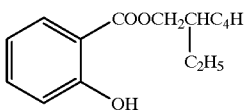

Other exemplary salicylic acid derivatives according to the present invention are the salicylic compounds or mixtures thereof with a branched alkyl chain corresponding to the following structural formula (I):

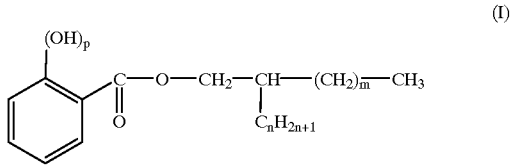

in which m has the value 5, 7 or 9, n has the value 4, 6 or 8 and p has the value 0 or 1, with the proviso that, when p has the value 0, then m has the value 5 or 7 and n has the value 4 or 6.

These compounds and process for the preparation thereof are described in U.S. Pat. No. 5,783,173. Exemplary compounds of formula (I) are 2-butyloctyl benzoate, 2-hexyldecyl benzoate, 2-butyloctyl hydroxybenzoate or mixtures thereof and more particularly the 2-butyloctyl benzoate/2-hexyldecyl benzoate mixture, such as the commercial product "Allstar AB" marketed by C. P. Hall, or 2-butyloctyl hydroxybenzoate, such as the commercial product "Hallbrite BHB" marketed by C. P. Hall.

The cinnamic acid derivative or derivatives and/or the salicylic acid derivative or derivatives of the invention are advantageously present in the final compositions in amounts ranging from 0.1% to 20% by weight and preferably from 0.2% to 15% by weight with respect to the total weight of the composition.

According to an essential characteristic of the compositions according to the invention, these cinnamic acid/ salicylic acid compounds must be present, alone or in admixtures, in an amount such that it is sufficient to dissolve, by itself alone, all, or substantially all, of the screening agent or agents of the silicon derivative substituted by a benzotriazole functional group in the composition. This minimum amount of solvent(s), intended to ensure complete and stable dissolution of the solid screening agent or agents of the invention, can be determined conventionally from the solubility parameters of said screening agents in these solvents.

For example, it has been determined that, at room temperature, the benzotriazole silicone corresponding to the compound (a) described above is soluble in a proportion of 50% by weight in 2-ethylhexyl p-methoxycinnamate (solvent screening agent of the cinnamate type) and in a proportion of 60% by weight in octyl salicylate (solvent screening agent of the salicylate type).

In general, it should be appreciated that the concentrations of silicon derivatives substituted with a benzotriazole functional group and of cinnamate and/or salicylate compounds are selected such that the sun protection factor of the final composition is preferably at least 2.

In a particularly preferred embodiment of the compositions in accordance with the invention, these preferably comprise no, or substantially no, solubilizer for the silicone derivatives bearing a benzotriazole functional group substituent, other than the sunscreen cinnamic acid derivatives or the sunscreen salicylic acid derivatives described above. According to the invention, it is considered that a given compound does not have solubilizing properties with respect to another given compound when the latter compound exhibits a solubility of less than about 1% by weight in this first compound.

In another preferred embodiment of the present invention, the cosmetically acceptable vehicle into which the various screening systems are formulated is an emulsion of oil-in-water type.

The compositions in accordance with the invention can also contain one or more additional hydrophilic or lipophilic sunscreens which are active in the UVA and/or UVB range (absorbers) other than, of course, the lipophilic screening agents indicated above. These additional screening agents are advantageously selected, in particular, from among cinnamic derivatives, salicylic derivatives, camphor derivatives, triazine derivatives, benzophenone derivatives, dibenzoylmethane derivatives, β,β-diphenylacrylate derivatives, p-aminobenzoic acid derivatives and the screening polymers and screening silicones described in WO-93/04665. Other examples of organic screening agents are set forth in EP-A-0,487,404.

Too, the compositions according to the invention can contain agents for artificially tanning and/or browning the skin (self-tanning agents), such as, for example, dihydroxyacetone (DHA).

The cosmetic compositions of this invention can also contain coated or uncoated metal oxide pigments or nanopigments (average size of the primary particles: generally ranging from 5 nm to 100 nm, preferably from 10 to 50 nm), such as, for example, titanium dioxide (amorphous or crystallized in rutile and/or anatase form), iron oxide, zinc oxide, zirconium oxide or cerium oxide, which are all photoprotective agents that are per se well known and which act by physically blocking out (reflection and/or scattering) the UV radiation. Conventional coating agents are, moreover, alumina and/or aluminum stearate. Such coated or uncoated metal oxide nanopigments are described, in particular, in EP-A-0,518,772 and EP-A-0,518,773.

The compositions of the invention can also comprise conventional cosmetic additives and adjuvants selected, in particular, from among fatty substances, organic solvents, ionic or nonionic thickeners, softeners, antioxidants and in particular free-radical-scavenging antioxidants, opacifiers, stabilizers, emollients, silicones, fluoro compounds, α-hydroxy acids, antifoaming agents, hydrating agents, vitamins, fragrances, preservatives, surfactants, pigments, fillers, sequestering agents, polymers, propellants, basifying or acidifying agents, dyes, colorants, or any other ingredient usually included in sunscreen cosmetics formulated as emulsions.

Suitable fatty substances may comprise an oil or a wax, or mixtures thereof, as well as fatty acids, fatty alcohols and fatty acid esters. The oils are advantageously selected from among animal, vegetable, mineral or synthetic oils and, in particular, from among liquid petrolatum, liquid paraffin, volatile or non-volatile silicone oils, isoparaffins, poly-α-olefins or fluorinated and perfluorinated oils. The waxes are likewise selected from among animal, fossil, vegetable, mineral or synthetic known waxes.

Lower alcohols and polyols are exemplary organic solvents.

The thickeners are advantageously selected from among, in particular, crosslinked acrylic acid homopolymers, guar gums and celluloses, which either may or may not be modified, such as hydroxypropylated guar gum, methylhydroxyethyl-cellulose, hydroxypropylmethyl cellulose or hydroxyethylcellulose.

Of course, one skilled in this art will take care to select this or these optional additional compounds and/or the amounts thereof such that the advantageous properties, in particular the sun protection factors obtained, intrinsically associated with the combination of screening agents in accordance with the invention are not, or not substantially, adversely affected by the envisaged addition or additions.

The compositions of the invention are easily prepared according to techniques which are well known to this art, in particular those intended for the formulation of emulsions of oil-in-water or water-in-oil type.

The subject compositions can be formulated, in particular, as a simple or complex emulsion (O/W, W/O, O/W/O or W/O/W), such as a cream, a milk, a lotion, an ointment, a gel or a cream gel, a salve, a powder or a solid stick and can optionally be packaged as an aerosol and can be provided in the form of a foam or of a spray.

When formulated as an emulsion, the aqueous phase thereof can comprise a nonionic vesicular dispersion prepared according to known techniques (Bangham, Standish and Watkins, J. Mol. Biol., 13, 238 (1965), FR-2,315,991 and FR-2,416,008).

The cosmetic compositions according to the invention are useful antisun/sunscreen or makeup products for photoprotecting the skin and/or the hair against the harmful effects of UV radiation. These products can be formulated as a suspension or dispersion in solvents or fatty substances, as a nonionic vesicle dispersion or, alternatively, as an emulsion, preferably of oil-in-water type, such as a cream or a milk, or as a salve, a salve, a gel, a lotion, a cream-gel, a solid tube such as a stick, an aerosol foam or a spray.

The cosmetic compositions according to the invention can also be used for protecting the hair and can be formulated as a shampoo, a lotion, a gel, an emulsion, a nonionic vesicle dispersion, a rinse-out composition to be applied before or after shampooing, before or after dyeing or bleaching, before, during or after a permanent-waving or hair-straightening operation, a styling or treating lotion or gel, a blow-drying or hairsetting lotion or gel or a composition for permanent-waving, straightening, dyeing or bleaching the hair.

When the composition is a makeup product for the eyelashes, eyebrows or skin, such as a skin treatment cream, foundation, lipstick, eye shadow, face powder, mascara or eye liner, it can be formulated in the anhydrous or aqueous, solid or pasty form, such as oil-in-water or water-in-oil emulsions, nonionic vesicular dispersions or else suspensions.

By way of example, in antisun formulations in accordance with the invention which comprise a vehicle of oil-in-water emulsion type, the aqueous phase (comprising in particular the hydrophilic screening agents) generally constitutes from 50% to 95% by weight, preferably from 70% to 90% by weight, of the total weight of the formulation, the oily phase (comprising in particular the lipophilic screening agents) from 5% to 50% by weight, preferably from 10% to 30% by weight, also with respect to the total weight of the formulation, and the (co)emulsifier(s) from 0.5% to 20% by weight, preferably from 2% to 10% by weight, again with respect to the total weight of the formulation.

As above indicated, the present invention also features a cosmetic regime or regimen for the skin or the hair for photoprotecting same against the deleterious effects of UV irradiation and which entails topically applying an effective amount of a cosmetic composition consistent herewith onto the skin or the hair.

In order to further illustrate the present invention and the advantages thereof, the following specific examples are given, it being understood that same are intended only as illustrative and in nowise limitative.

EXAMPLE 1

Antisun Cream (Oil/Water Emulsion)

| | |
|---|---|
| Benzotriazole silicone corresponding to the composition (a) | 5 g |
| 2-Ethylhexyl cinnamate (Parsol MCX) | 10 g |
| Emulsifier (Arlacel 165) | 2 g |
| Stearic acid | 2.5 g |
| Preservative q.s. | |
| Stearyl alcohol | 0.5 g |
| Triethanolamine | 0.5 g |
| Moisturizers | 8 g |
| Preservative q.s. | |
| Sequestering agent | 0.1 g |
| Acrylic thickening polymer (Pemulen TR1) | 0.22 g |
| Polydimethylsiloxane (DC245 Fluid) | 2 g |
| Triethanolamine | 0.22 g |
| Purified water q.s | 100 g |

The above emulsion was formulated by dissolving the screening agents in the fatty phase, by then adding the emulsifiers to this fatty phase, heated to approximately 80° C., and finally by adding, with rapid stirring, the water heated beforehand to the same temperature.

EXAMPLE 2

| | |
|---|---|
| Benzotriazole silicone corresponding to the composition (a) | 6 g |
| Octyl salicylate | 10 g |
| Emulsifier (Arlacel 165) | 2 g |
| Stearic acid | 2.5 g |
| Preservative q.s. | |
| Stearyl alcohol | 0.5 g |
| Triethanolamine | 0.5 g |
| Moisturizers | 8 g |
| Preservative q.s. | |
| Sequestering agent | 0.1 g |
| Acrylic thickening polymer (Pemulen TR1) | 0.22 g |
| Polydimethylsiloxane (DC245 Fluid) | 2 g |
| Triethanolamine | 0.22 g |
| Purified water q.s | 100 g |

The above emulsion was formulated by dissolving the screening agents in the fatty phase, by then adding the emulsifiers to this fatty phase, heated to approximately 80° C., and finally by adding, with rapid stirring, the water heated beforehand to the same temperature.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable cosmetic/dermatological sunscreen composition suited for the UV-photoprotection of human skin and/or hair, comprising (i) a UV-photoprotecting effective amount of at least one solubilized organolipophilic silicon compound bearing a benzotriazole function substituent and (ii) an amount of at least one cinnamic acid sunscreen compound and/or at least one salicylic acid sunscreen compound effective to dissolve said at least one organolipophilic silicon compound.

2. The cosmetic/dermatological sunscreen composition as defined by claim 1, comprising an effective amount of at least one liquid cinnamic acid sunscreen compound and/or at least one liquid salicylic acid compound to itself or themselves substantially dissolve the total UV-photoprotecting effective amount of said at least one organolipophilic silicon compound.

3. The cosmetic/dermatological sunscreen composition as defined by claim 2, formulated into a topically applicable, cosmetically/dermatologically acceptable vehicle, diluent or carrier therefor.

4. The cosmetic/dermatological sunscreen composition as defined by claim 1, said at least one organolipophilic benzotriazole-substituted silicon compound comprising at least one structural unit having the formula (1):

in which $R_1$ is an optionally halogenated $C_1$–$C_{10}$ alkyl radical, or a phenyl or trimethylsilyloxy radical; a is an integer ranging from 0 to 3, inclusive; and the symbol G is a monovalent radical directly bonded to a silicon atom and having the structural formula (2) below:

(2)

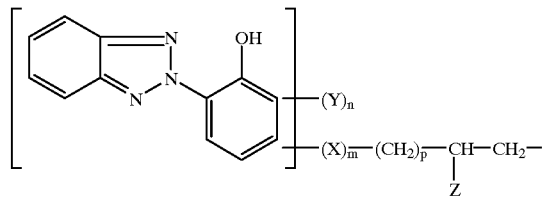

in which the radicals Y, which may be identical or different, are each a $C_1$–$C_8$ alkyl radical, a halogen atom, or a $C_1$–$C_4$ alkoxy radical, with the proviso that, in the latter instance, two adjacent groups Y on the same aromatic ring member can together form an alkylidenedioxy group wherein the alkylidene group contains 1 or 2 carbon atoms; X is O or NH; Z is hydrogen or a $C_1$–$C_4$ alkyl radical; n is an integer ranging from 0 to 3, inclusive; m is 0 or 1; and p is an integer ranging from 1 to 10, inclusive.

5. The cosmetic/dermatological sunscreen composition as defined by claim 4, said at least one organolipophilic benzotriazole-substituted silicon compound having the structural formula (5) or (6):

(5)

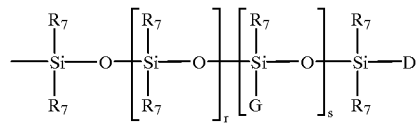

or (6)

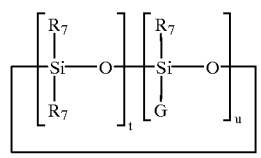

in which the radicals $R_7$, which may be identical or different, are each a $C_1$–$C_{10}$ alkyl, phenyl, 3,3,3-trifluoropropyl or trimethylsilyloxy radical, at least 80% by number of the radicals $R_7$ being methyl radicals; the radicals D, which may be identical or different, are each a radical $R_7$ or the radical G; r is an integer ranging from 0 to 50, inclusive, and s is an integer ranging from 0 to 20 inclusive, and if s=0, at least one of the two radicals D is a radical G; u is an integer ranging from 1 to 6, inclusive, and t is an integer ranging from 0 to 10, inclusive, with the proviso that t+u is greater than or equal to 3.

6. The cosmetic/dermatological sunscreen composition as defined by claim 5, said at least one organolipophilic benzotriazole-substituted silicon compound having the structural formula (7):

(7)

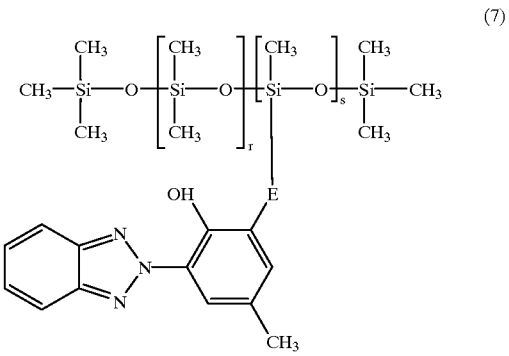

in which $0 \leq r \leq 10$; $1 \leq s \leq 10$; and E is the divalent radical:

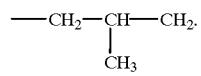

7. The cosmetic/dermatological sunscreen composition as defined by claim 5, said at least one organolipophilic benzotriazole-substituted silicon compound having the structural formula:

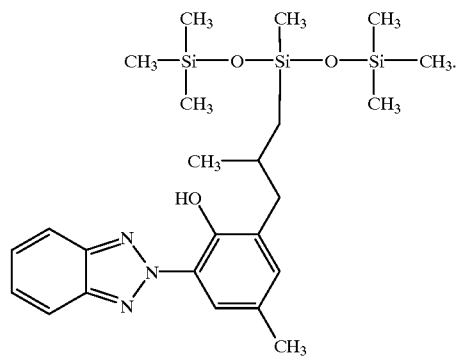

8. The cosmetic/dermatological sunscreen composition as defined by claim 1, comprising from 0.1% to 20% by weight of said at least one organolipophilic benzotriazole-substituted silicon compound.

9. The cosmetic/dermatological sunscreen composition as defined by claim 8, comprising from 0.2% to 15% by weight of said at least one organolipophilic benzotriazole-substituted silicon compound.

10. The cosmetic/dermatological sunscreen composition as defined by claim 1, comprising at least one cinnamic acid sunscreen compound selected from among isopentyl 4-methoxycinnamate, 2-ethylhexyl 4-methoxycinnamate, methyl diisopropylcinnamate, isoamyl 4-methoxycinnamate and diethanolamine 4-methoxycinnamate.

11. The cosmetic/dermatological sunscreen composition as defined by claim 10, comprising 2-ethylhexyl p-methoxycinnamate having the following structural formula:

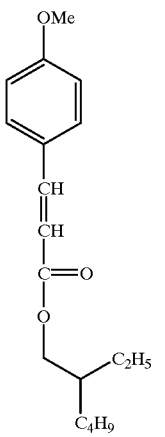

12. The cosmetic/dermatological sunscreen composition as defined by claim 1, comprising at least one sunscreen compound selected from among homomenthyl salicylate, 2-ethylhexyl salicylate, triethanolamine salicylate and 4-isopropylbenzyl salicylate.

13. The cosmetic/dermatological sunscreen composition as defined by claim 12, comprising homomenthyl salicylate having the following structural formula:

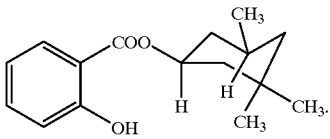

14. The cosmetic/dermatological sunscreen composition as defined by claim 12, comprising octyl salicylate having the following structural formula:

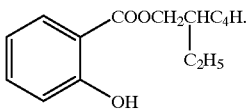

15. The cosmetic/dermatological sunscreen composition as defined by claim 1, comprising at least one salicylic acid sunscreen compound including a branched alkyl chain and having the following structural formula (I):

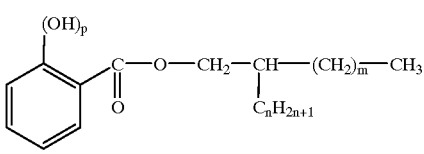

in which m has the value 5, 7 or 9, n has the value 4, 6 or 8 and p has the value 0 or 1, with the proviso that, when p has the value 0, then m has the value 5 or 7 and n has the value 4 or 6.

16. The cosmetic/dermatological sunscreen composition as defined by claim 15, comprising 2-butyloctyl benzoate, 2-hexyldecyl benzoate, 2-butyloctyl hydroxybenzoate or mixture thereof.

17. The cosmetic/dermatological sunscreen composition as defined by claim 1, comprising from 0.1% to 20% by weight of said at least one cinnamic acid sunscreen compound and/or at least one salicylic acid sunscreen compound.

18. The cosmetic/dermatological sunscreen composition as defined by claim 17, comprising from 0.2% to 15% by weight of said at least one cinnamic acid sunscreen compound and/or at least one salicylic acid sunscreen compound.

19. The cosmetic/dermatological sunscreen composition as defined by claim 1, having a sun protection factor of at least 2.

20. The cosmetic/dermatological sunscreen composition as defined by claim 1, devoid, or substantially devoid, of any solubilizing agent for said at least one organolipophilic benzotriazole-substitute silicon compound other than said at least one cinnamic acid sunscreen compound and/or said at least one salicylic acid sunscreen compound.

21. The cosmetic/dermatological sunscreen composition as defined by claim 1, comprising an oil-in-water emulsion.

22. The cosmetic/dermatological sunscreen composition as defined by claim 1, comprising a water-in-oil emulsion.

23. The cosmetic/dermatological sunscreen composition as defined by claim 1, further comprising at least one additional hydrophilic or lipophilic UVA- and/or UVB-sunscreen.

24. The cosmetic/dermatological sunscreen composition as defined by claim 23, further comprising at least one cinnamic sunscreen, salicylic sunscreen, camphor sunscreen, benzophenone sunscreen, dibenzoylmethane sunscreen, triazine sunscreen, β,β'-diphenylacrylate sunscreen, p-aminobenzoic acid sunscreen, sunscreen polymer and/or sunscreen silicone other than one benzotriazole-substituted.

25. The cosmetic/dermatological sunscreen composition as defined by claim 1, further comprising at least one active agent for the artificial tanning and/or browning of human skin.

26. The cosmetic/dermatological sunscreen composition as defined by claim 1, further comprising at least one cosmetically/dermatologically acceptable adjuvant or additive.

27. The cosmetic/dermatological sunscreen composition as defined by claim 26, said at least one adjuvant or additive comprising a fat, organic solvent, ionic or nonionic thickening agent, softener, antioxidant, anti-free-radical antioxidant, opacifying agent, stabilizing agent, emollient, silicone, fluoro compound, hydroxy acid, antifoaming agent, vitamin, fragrance, preservative, surfactant, filler, sequestering agent, hydrating agent, polymer, propellant, basifying or acidifying agent, dye, colorant, or mixture thereof.

28. The cosmetic/dermatological sunscreen composition as defined by claim 1, further comprising a photoprotecting effective amount of particulates of at least one inorganic pigment or nanopigment.

29. The cosmetic/dermatological sunscreen composition as defined by claim 28, said at least one pigment or nanopigment comprising titanium dioxide, zinc oxide, iron oxide, zirconium oxide, cerium oxide, or mixture thereof.

30. The cosmetic/dermatological sunscreen composition as defined by claim 1, comprising a nonionic vesicle dispersion, lotion, cream, milk, gel, salve, cream gel, ointment, suspension, dispersion, powder, solid stick, foam or spray.

31. The cosmetic/dermatological sunscreen composition as defined by claim 1, comprising a makeup.

32. The cosmetic/dermatological sunscreen composition as defined by claim 1, comprising a liquid, solid or paste.

33. The cosmetic/dermatological sunscreen composition as defined by claim 1, comprising a shampoo, rinse, styling lotion or gel, blow-drying or hairsetting lotion or gel, or permanent-waving, straightening, dyeing or bleaching composition for the hair.

34. The cosmetic/dermatological sunscreen composition as defined by claim 1, comprising a foundation, lipstick, mascara, eyeshadow, or eyeliner.

35. A regime/regimen for photoprotecting human skin and/or hair against the deleterious effects of ultraviolet radiation, comprising topically applying thereto an effective amount of the cosmetic/dermatological sunscreen composition as defined by claim 1.

36. A regime/regimen for photoprotecting human skin and/or hair against the deleterious effects of solar radiation, comprising topically applying thereto an effective amount of the cosmetic/dermatological sunscreen composition as defined by claim 1.

* * * * *